United States Patent
Wu

(10) Patent No.: US 10,606,064 B2
(45) Date of Patent: Mar. 31, 2020

(54) OPTICAL PROBES WITH ASTIGMATISM CORRECTION

(71) Applicant: Canon U.S.A., Inc., Melville, NY (US)

(72) Inventor: Tzu-Yu Wu, Malden, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/879,283

(22) Filed: Jan. 24, 2018

(65) Prior Publication Data

US 2019/0227297 A1  Jul. 25, 2019

(51) Int. Cl.

| G02B 23/24 | (2006.01) |
|---|---|
| G02B 23/26 | (2006.01) |
| G02B 23/06 | (2006.01) |
| G01B 9/02 | (2006.01) |
| A61B 1/00 | (2006.01) |
| A61B 5/00 | (2006.01) |
| A61B 1/002 | (2006.01) |

(52) U.S. Cl.
CPC .......... *G02B 23/2423* (2013.01); *A61B 1/002* (2013.01); *A61B 1/00096* (2013.01); *A61B 5/0066* (2013.01); *A61B 5/0071* (2013.01); *A61B 5/0084* (2013.01); *G01B 9/0205* (2013.01); *G02B 23/06* (2013.01); *G02B 23/26* (2013.01)

(58) Field of Classification Search
None
See application file for complete search history.

(56) References Cited

U.S. PATENT DOCUMENTS

| 5,554,100 | A | 9/1996 | Leiner et al. |
|---|---|---|---|
| 6,433,937 | B1 | 8/2002 | Konno |
| 6,445,939 | B1 | 9/2002 | Swanson |
| 6,501,878 | B2 | 12/2002 | Hughes |
| 6,564,087 | B1 * | 5/2003 | Pitris ................ A61B 1/00172 600/478 |
| 6,801,375 | B2 | 10/2004 | Hayashide |
| 6,954,296 | B2 | 10/2005 | Takakubo |
| 7,366,376 | B2 | 4/2008 | Shishkov |

(Continued)

FOREIGN PATENT DOCUMENTS

| JP | H04-60608 A | 2/1992 |
|---|---|---|
| JP | H7-171162 A | 7/1995 |

(Continued)

OTHER PUBLICATIONS

Yu-Kuan Lu et al., Asymmetric elliptic-cone-shaped microlens for efficient coupling to high-power laser diodes, Optics Express, vol. 15, No. 4, Feb. 19, 2007.

(Continued)

*Primary Examiner* — Tina M Wong
(74) *Attorney, Agent, or Firm* — Canon U.S.A., Inc. I.P. Division

(57) ABSTRACT

A device comprises a light-guiding component, an optical component, and a light-reflecting component that is configured to receive light from the optical component and direct the light along a path. Also, at least one of the optical component and the light-reflecting component has an optical power in a tangential direction or a sagittal direction that compensates for a negative power of a sheath in the tangential direction to correct for aberration.

30 Claims, 18 Drawing Sheets

(56) References Cited

U.S. PATENT DOCUMENTS

| | | | |
|---|---|---|---|
| 7,457,044 B2 | 11/2008 | Ohzawa | |
| 7,492,987 B2 * | 2/2009 | Yeik | A61B 18/24 385/31 |
| 7,680,378 B2 | 3/2010 | Alphonse | |
| 7,813,609 B2 | 10/2010 | Petersen | |
| 8,180,134 B2 | 5/2012 | Wang | |
| RE43,875 E | 12/2012 | Shishkov | |
| 8,425,500 B2 * | 4/2013 | Hanley | A61B 18/24 29/426.2 |
| 8,515,221 B2 | 8/2013 | Flanders | |
| 8,582,934 B2 | 11/2013 | Adler | |
| 8,781,287 B2 | 7/2014 | Flanders | |
| 8,971,679 B2 | 3/2015 | Ho | |
| RE45,512 E | 5/2015 | Tearney | |
| 9,036,966 B2 * | 5/2015 | Bhagavatula | G02B 6/32 385/33 |
| 9,069,122 B2 | 6/2015 | Takeuchi | |
| 9,087,368 B2 | 7/2015 | Tearney | |
| 9,164,272 B2 | 10/2015 | Maillard | |
| 9,318,810 B2 | 4/2016 | Zelenski | |
| 9,488,782 B2 * | 11/2016 | Griffin | G02B 6/262 |
| 9,662,173 B1 * | 5/2017 | Griffin | A61B 18/24 |
| 10,234,676 B1 | 3/2019 | Elmaanaoui | |
| 2002/0076180 A1 | 6/2002 | Miyano | |
| 2004/0133071 A1 | 7/2004 | Alekseenko et al. | |
| 2005/0165315 A1 | 7/2005 | Zuluaga | |
| 2006/0067620 A1 | 3/2006 | Shishkov | |
| 2007/0159601 A1 * | 7/2007 | Ho | G02C 7/02 351/221 |
| 2007/0233396 A1 | 10/2007 | Tearney | |
| 2008/0013960 A1 | 1/2008 | Tearney | |
| 2009/0244545 A1 * | 10/2009 | Toida | A61B 5/0066 356/477 |
| 2009/0262361 A1 | 10/2009 | Tanioka et al. | |
| 2009/0306477 A1 | 12/2009 | Togino | |
| 2010/0253949 A1 * | 10/2010 | Adler | A61B 5/0066 356/479 |
| 2011/0137124 A1 | 6/2011 | Milner | |
| 2011/0141759 A1 | 6/2011 | Smith | |
| 2012/0101374 A1 * | 4/2012 | Tearney | A61B 5/0066 600/427 |
| 2013/0235176 A1 | 9/2013 | Miyano | |
| 2014/0288417 A1 | 9/2014 | Schmidtlin et al. | |
| 2015/0025369 A1 | 1/2015 | Bhagavatula et al. | |
| 2015/0378105 A1 | 12/2015 | Godbout et al. | |
| 2016/0274345 A1 | 9/2016 | Ueno et al. | |
| 2016/0299170 A1 | 10/2016 | Ito et al. | |
| 2017/0168232 A1 | 6/2017 | Tearney et al. | |
| 2017/0235126 A1 | 8/2017 | DiDomenico | |
| 2018/0070932 A1 | 3/2018 | Tearney et al. | |
| 2018/0256032 A1 | 9/2018 | Takeuchi et al. | |
| 2019/0196188 A1 | 6/2019 | Hirata et al. | |
| 2019/0223699 A1 * | 7/2019 | Wu | A61B 1/00188 |
| 2019/0223700 A1 | 7/2019 | Elmaanaoui | |
| 2019/0227297 A1 * | 7/2019 | Wu | G02B 23/2423 |
| 2019/0227298 A1 | 7/2019 | Elmaanaoui | |

FOREIGN PATENT DOCUMENTS

| | | |
|---|---|---|
| JP | 2010-533049 A | 10/2010 |
| JP | 2011-147705 A | 8/2011 |
| JP | 2012-229976 A | 11/2012 |
| JP | 2015-532179 A | 11/2015 |
| WO | 2015116939 A1 | 8/2015 |
| WO | 2016077252 A1 | 5/2016 |

OTHER PUBLICATIONS

SPIE, Gradient Index Lens, Optipedia, Internet Archive Wayback Machine, May 16, 2016, downloaded from http://web.archive.org/web/20160516035942/http://spie.org/publications/tt48_55_gradient_index_lens.

Zhen Qiu et al., New Endoscopic Imaging Technology Based on MEMS Sensors and Actuators, Micromachines 2017, Jul. 2017.

Tianshi Wang et al., Numerical Analysis of Astigmatism Correction in Gradient Refractive Index Lens Based Optical Coherence Tomography Catheters, Applied Optics, 51(21):5244-5252, Jul. 20, 2012.

Woonggyu Jung et al., Numerical Analysis of Gradient Index Lens-Based Optical Coherence Tomography Imaging Probes, Journal of Biomedical Optics, vol. 15(6), Nov. 2010.

D. Yelin et al., Three-dimensional miniature endoscopy, Nature, Oct. 19, 2006, pp. 765—vol. 443.

Max Born, et al., Priciples of Optics: Electromagnetic Theory of Propagation, Interference and Diffraction of Light, 6th ed., Pergamon Press, 1980, pp. 169-174 and 214-217 (and title and copyright pages included) (The year of publication for this reference is sufficiently earlier than the effective U.S. filing date and any foreign priority date so that the particular month of publication is not in issue.).

Eugene Hecht, Optics, 4th ed., Pearson Education, Adelphi University, 2002, pp. 261-264 (and title and copyright pages included) (The year of publication for this reference is sufficiently earlier than the effective U.S. filing date and any foreign priority date so that the particular month of publication is not in issue.).

Frank L. Pedrotti, et al., Introduction to Optics, 2nd ed, Prentice-Hall, Inc., Upper Saddle River, New Jersey, 1993, pp. 98-100 (and title and copyright pages included) (The year of publication for this reference is sufficiently earlier than the effective U.S. filing date and any foreign priority date so that the particular month of publication is not in issue.).

* cited by examiner

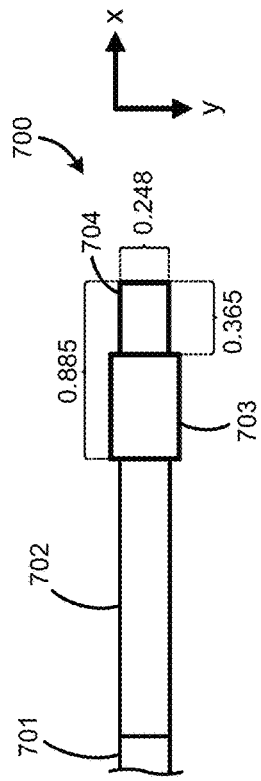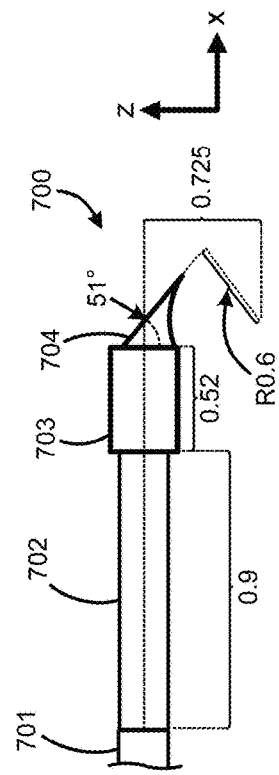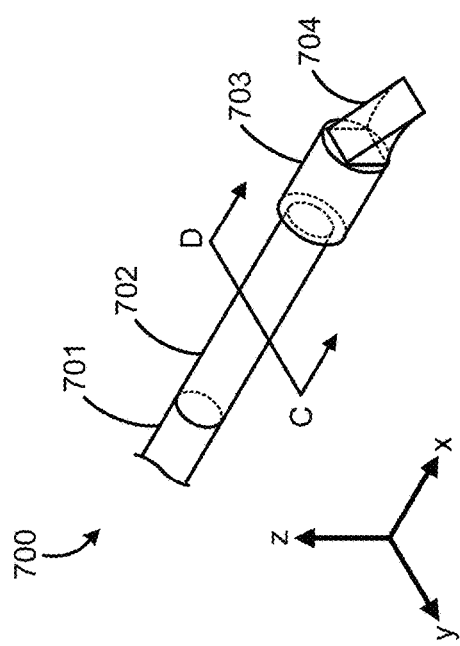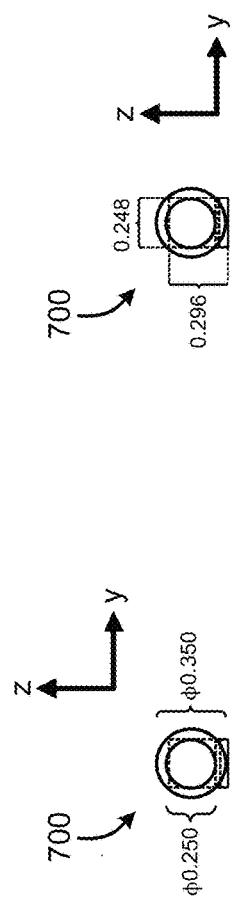

OPTICAL PROBES WITH ASTIGMATISM CORRECTION

BACKGROUND

This application generally concerns optical probes.

A catheter's optical system is usually fragile and is therefore protected by a sheath. Astigmatism is created in the optical system by the cylindrical shape of the sheath. Astigmatism causes the foci of the beams of light in two orthogonal directions to converge at different distances with different beam sizes or to diverge in one direction while converging in another direction. Consequently, the image quality of the optical system is degraded.

SUMMARY

Some embodiments of an optical probe comprise a first light-guiding component, a second light-guiding component, a lens, and a light-reflecting component that is configured to receive light from the lens and direct the light along a path. At least one of the light-guiding component and the light-reflecting component has an optical power in one of a tangential direction or a sagittal direction.

Some embodiments of a device comprise a sheath and an optical probe that includes a first light-guiding component, a second light-guiding component, a lens, and a light-reflecting component. Also, the optical probe has an optical power in a tangential direction.

Some embodiments of a device comprise a lens and a light-reflecting component that has an optical power in one of a tangential direction or a sagittal direction.

Some embodiments of an optical probe comprise an optical fiber, a spacer, a lens, a light-reflecting component that is configured to receive light from the lens and direct the light along a path, and a correction element. The correction element includes a material that is at least partially transparent. Also, the correction element has an asymmetric optical power, and the correction element lies along the path such that the light from light-reflecting component travels through the material that is at least partially transparent.

Some embodiments of an optical probe comprise a first light-guiding component, a second light-guiding component, a lens, a light-reflecting component that is configured to receive light from the lens and direct the light along a path, and a correction element. The correction element has an optical power in a tangential direction, and the correction element lies along the path such that correction element transmits the light from light-reflecting component.

BRIEF DESCRIPTION OF THE DRAWINGS

FIGS. 7A-7E illustrate an example embodiment of an optical probe and a sheath.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Some optical probes (e.g., endoscopes) are configured to capture images from inside a subject, such as a human patient. These optical probes may include a fiber probe and include both a lens and a mirror at a distal tip of the fiber probe. The lens and the mirror focus a beam of light, collect the beam of light, and guide the beam of light. Also, one or more optical fibers in the fiber probe can be used to navigate the optical probe to a sample (e.g., organs, tissues), deliver light to the sample, and receive light from the sample.

For example, some optical probes that are configured to perform optical coherence tomography (OCT) can capture depth-resolved images of blood vessels. These optical probes may be inside a catheter that includes a sheath and a coil. As the beam of light from the optical probe is rotated across the surface of a blood vessel, cross-sectional images of the blood vessels in the surface are obtained. In order to acquire three-dimensional data, the optical probe can be translated longitudinally during the rotation to obtain images from a helical-scanning pattern. This helical scanning may be performed by pulling the tip of the optical probe back towards a proximal end while the optical probe is being rotated.

The catheter may include a transparent sheath, through which a beam of light from the optical probe passes. The smaller the diameter of the transparent sheath, the stronger the dioptric power that the transparent sheath adds along one axis of the optical system, and the greater the astigmatism of the optical system.

Figure 1:
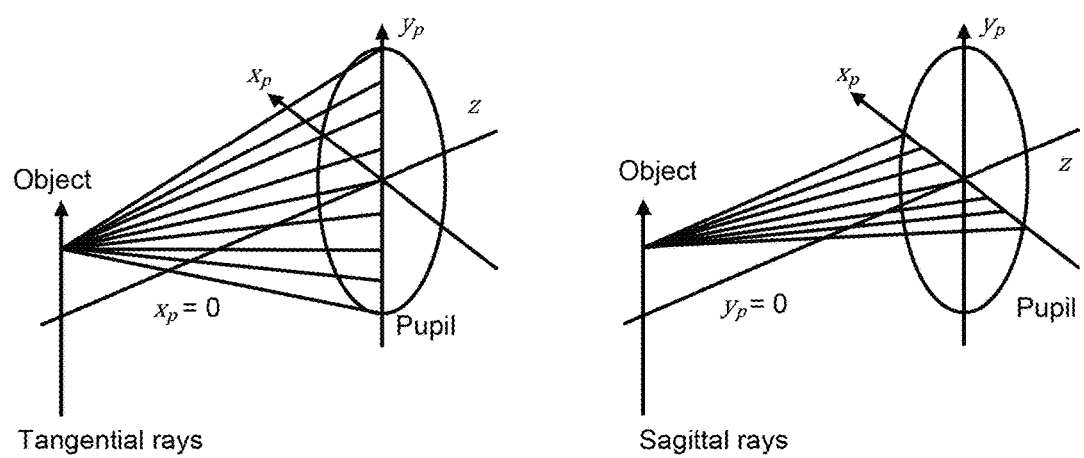
FIG. 1 illustrates ray definitions and a coordinate system.

FIG. 1 illustrates ray definitions and a coordinate system. Tangential rays intersect the pupil at $x_p=0$, while sagittal rays intersect the pupil at $y_p=0$. The following description uses these ray definitions.

Figure 2:
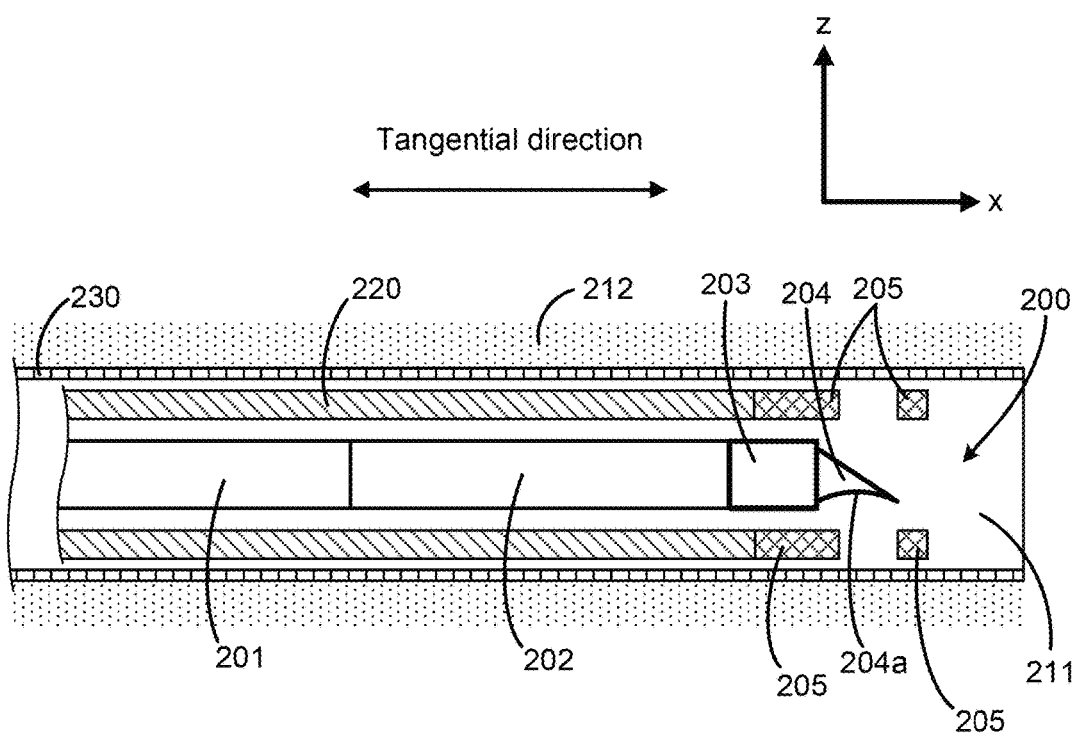
FIG. 2 illustrates a partially-cutaway view of an example embodiment of an optical probe, a drive cable, and a sheath.

FIG. 2 illustrates a partially-cutaway view of an example embodiment of an optical probe 200, a drive cable 220, and a sheath 230. The optical probe 200 includes a first light-guiding component 201 (e.g., single-mode optical fiber, multimode optical fiber, double-clad optical fiber), a second light-guiding component 202 (e.g., a glass rod), a lens 203 (e.g., a gradient-index (GRIN) lens), a light-reflecting component 204 (e.g., a prism), and a protector 205 (e.g., a CAN, an epoxy tube).

The second light-guiding component 202 may be a glass rod or another spacer that is adjustable to change the numerical aperture of the beam at the entrance of the lens 203. The interface between optical components may be tilted with an angle of 4°-8° to reduce back reflection from the interfaces. For example, the interface between the second light-guiding component 202 and the lens 203 may be tilted with an angle of 8°, and the interface between the lens 203 and the prism 204 may be titled with an angle of 4°-8° to reduce back reflection that may cause artifact(s) in an image (e.g., an OCT image). The lens 203 may be a GRIN lens that is attached to a proximal end of the light-reflecting component 204. Some embodiments of the optical probe 200 include an optical component that includes the second light-guiding component 202 (e.g., a glass rod, a spacer), the lens 203, or a combination of the second light-guiding component 202 and the lens 203.

The light-reflecting component 204 may have a total internal reflection (TIR) or a mirror-coated surface. Light exits the light-reflecting component 204 from an exiting surface 204a. The protector 205 has at least one opening, and light that travels between the light-reflecting component 204 and a sample passes through the at least one opening. Also, the sheath 230 contains an inner medium 211 (e.g., air, a contrast agent), which is the medium inside the sheath 230, and the sheath 230 is surrounded by an outer medium 212 (e.g., air, a contrast agent), which is the medium outside the sheath 230. In some embodiments, the inner media 211 is air with a refractive index of 1 (n=1), and the outer media 212 is a contrast agent with a refractive index of 1.45 (n=1.45).

The drive cable 220 and the optical probe 200 are fixed relative to each other. The drive cable 220 delivers torque from a proximal-end motor to a distal end in order to spin the distal end, which is attached to the optical probe 200. Spinning the optical probe 200 permits the optical probe to capture a 360° view. Within the sheath 230, the optical probe 200 can freely spin or rotate on its longitudinal axis without spinning or rotating the sheath 230. Accordingly, the sheath 230 can remain stationary while the optical probe 200 spins.

The first light-guiding component 201 and the second light-guiding component 202 can deliver beams of light in one or more different wavelengths to the distal tip of the optical probe 200. In some embodiments, the optical probe 200 emits two beams. One beam is used for OCT and, in some embodiments, this beam has the central wavelength of 1310 nm. The wavelength of the beam can be broadband, or the beam can be scanned in a bandwidth that is approximately 100 nm to 150 nm wide. The other beam has a wavelength of excitation for fluorescence (e.g., 633 nm). The incidence angle of the beam to the sheath 230 may be greater than 10° and less than 30° in air. Also, for the OCT wavelength or wavelengths, the focused beam position may be 1 mm to 3.5 mm away, as measured vertically from the optical axis of the optical probe 200. And fluorescence beam may focus outside of the sheath 230 close to the focus beam position of OCT wavelength. The length of the lens 203, the refractive-index profile of the lens 203, and the length of the second light-guiding component 202 are used to configure the beam width and the working distance to the desired values.

The light-reflecting component 204 has an exiting surface 204a (e.g., a concave surface) that has an optical power in the tangential direction or in the sagittal direction. The optical power of the exiting surface 204a compensates for or corrects the astigmatism that is caused by the sheath 230.

Figure 3:
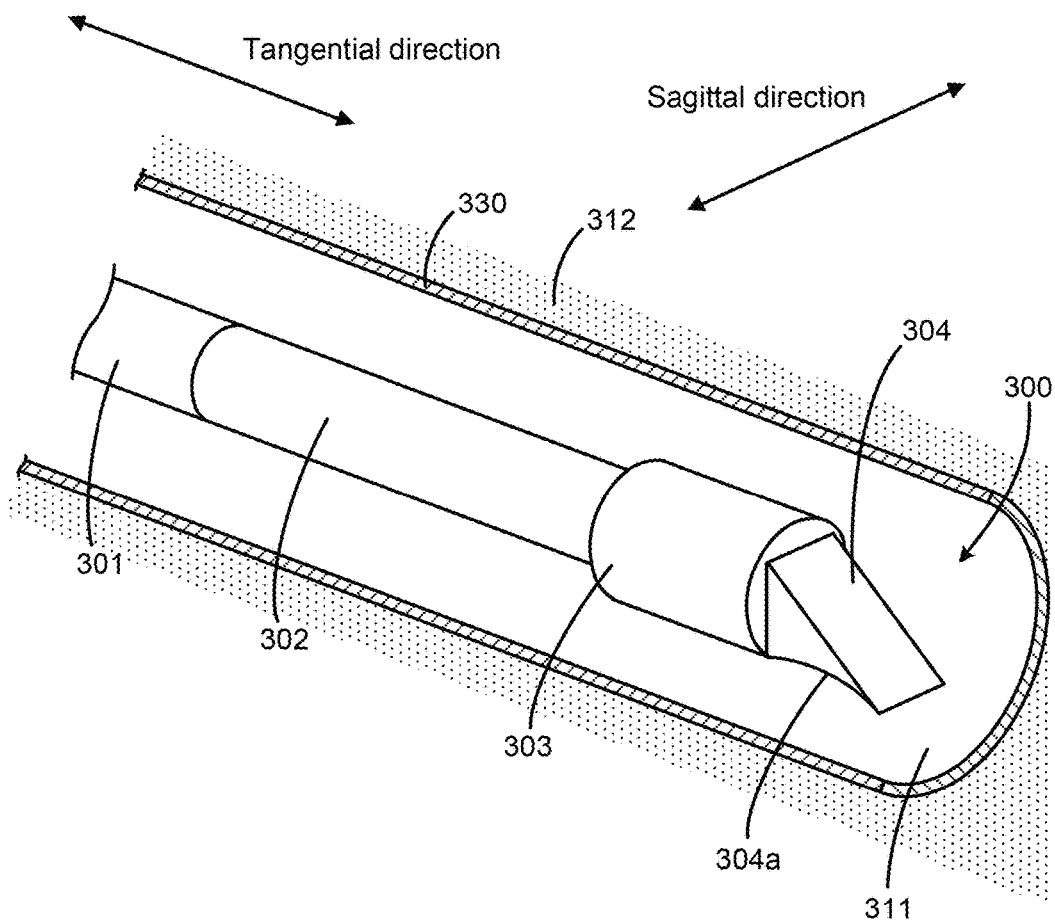
FIG. 3 illustrates a perspective view of an example embodiment of an optical probe and a sheath.
Figures 4A, 4B, 4C, 4D:
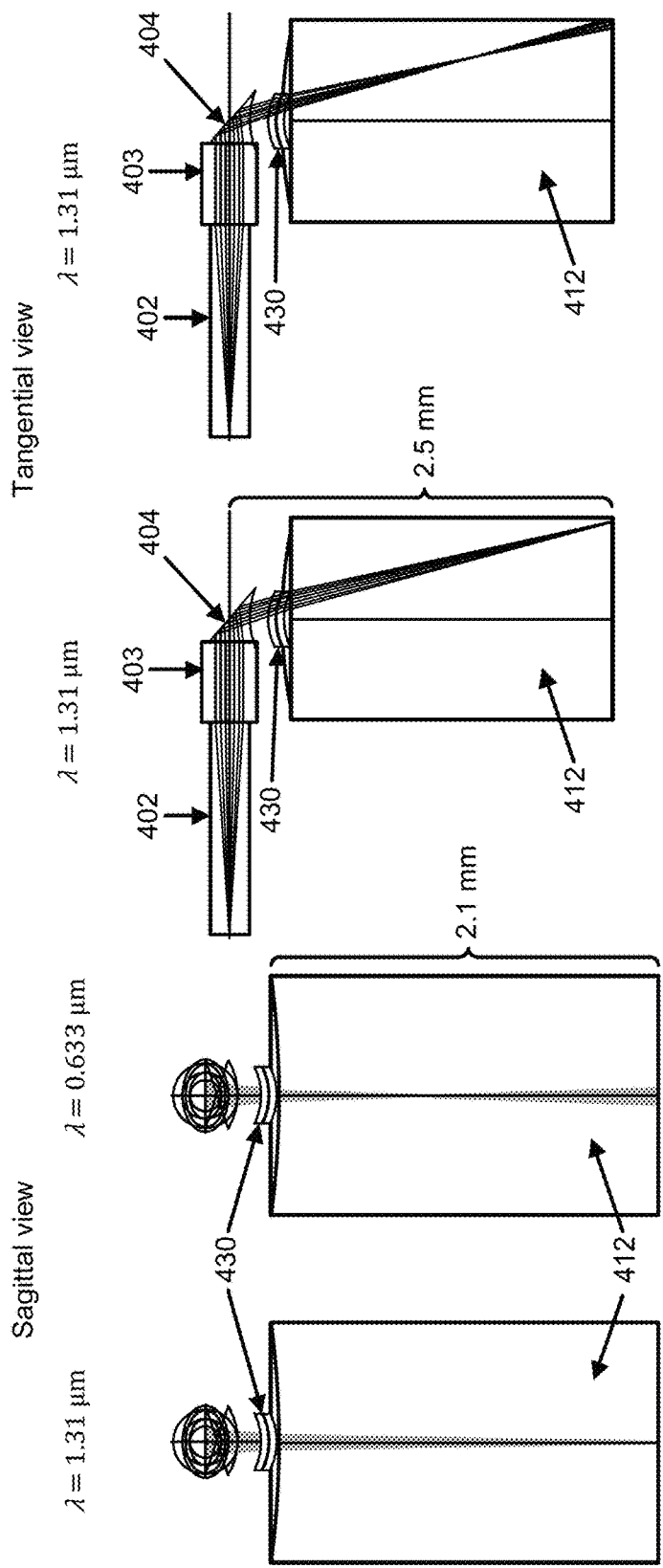
FIGS. 4A-D illustrate sagittal views and tangential views of an example embodiment of an optical probe and a sheath.

FIG. 3 illustrates a perspective view of an example embodiment of an optical probe 300 and a sheath 330. The optical probe 300 includes a first light-guiding component 301, a second light-guiding component 302, a lens 303, and a light-reflecting component 304. FIG. 3 omits the protector, although some embodiments of the optical probe 300 include a protector.

Because the sheath 330 has an optical power, the sheath 330 can cause astigmatism. For example, the sagittal optical power of the sheath is negative if $$(n_{sheath} - n_i) > \frac{R_{Si}}{R_{So}}(n_{sheath} - n_{ca}),$$

where $n_{sheath}$ is the refractive index of the sheath 330, where $n_i$ is the refractive index of the inner media 311 (e.g., air, a contrast agent), and where $n_{ca}$ is the refractive index of the outer media 312 (e.g., air, a contrast agent). Also, $R_{Si}$ is the inner radius of the sheath 330, and $R_{So}$ is the outer radius of the sheath 330. Thus, in embodiments where $n_{sheath}=1.5$, where $R_{Si}/R_{So}<1$, where either $n_i=1$ for air or $n_i=1.3$-1.45 for epoxy, and where $n_{ca}=1.45$, the above equation is satisfied (i.e., the sheath has a negative optical power).

In some embodiments, the astigmatism correction is accomplished by properly configuring the dimensions of the second light-guiding component 302, the dimensions of the lens 303, and the dimensions of the exiting surface 304a of the light-reflecting component 304.

Some embodiments of the optical probe 300 are configured for a multimodality system that simultaneously performs OCT imaging using light with a wavelength of 1.31 um and fluorescence mapping using light with a wavelength of 0.633 um. Depending on the specification of the imaging, it may be critical to focus the OCT wavelength, which can provide structural information, at a designed optimal working distance to provide lateral resolution, while the fluorescence wavelength is focused slightly off from the optimal working distance of the OCT imaging, thereby allowing the fluorescence wavelength to have a larger beam size with a lower lateral resolution at the optimal working distance of the OCT imaging.

For example, in coronary arteries, the diameters of the arteries of interest are often about 2 to 4 mm. Assuming that the optical probe 300 is located at the center of the artery, the radius of the artery corresponds to the working distance, and is 1 to 2 mm from the optical axis of the optical probe 300.

OCT and fluorescence wavelengths both penetrate the vessel, so, in some embodiments, the focus position or the working distance is optimal at 1 to 3 mm. Within these working distances, the focus may be different between the two modalities. Some embodiments of the optical probe 300 (e.g., for coronary-artery measurement) have focal distances or working distances that are within 2 mm of each other. Some embodiments have larger differences in the focal distances or working distances, for example embodiments that are used for larger blood vessels (e.g., peripheral arteries), corresponding to the blood vessel's diameter and the desired working distance.

The optimization of the focal point may be accomplished by using the refractive indices for the two wavelengths and solving the optimization problem. When optimizing, it may be efficient to add another material, with a different combination of refractive indices for the two wavelengths, by splitting one or more optical components or by adding a spacer.

Also, some embodiments of the optical probe 300 are configured for other modalities, such as near-infrared spectroscopy, in addition to or in alternative to OCT and fluorescence imaging.

FIGS. 4A-D illustrate sagittal views and tangential views of an example embodiment of an optical probe and a sheath. In this embodiment, light that has passed through a double-clad fiber that has a numerical aperture (NA) of 0.09 passes through a length of coreless fiber 402 (e.g., fused silica) that is approximately 0.9 mm long and then enters a GRIN lens 403 that has a length of 0.52 mm and a diameter of 350 µm. The light exits the lens 403 and is reflected by the reflecting surface of a prism 404, which has a tilt angle of 50±2° (i.e., the chief ray from the lens 403 has an incident angle of 50±2°) and a refractive index of 1.52 (n=1.52). Then the light passes through a cylindrical surface of the prism 404, which has an optical power only in the tangential direction, and then passes through a sheath 430, which has an optical power only in the sagittal direction. The curvature and refractive index of the prism 404 is configured such that the optical power of the prism 404 in the tangential direction is essentially the same as the optical power of the sheath 430 in the sagittal direction to achieve astigmatism correction. In some embodiments, the curvature and the refractive index of the prism 404 is configured to control the amount of astigmatism so as to achieve the desired numerical aperture and the desired working distance in tangential direction. In air, the chief ray has an incident angle of 20° to the sheath 430. After exiting the sheath 430, the light then passes through a contrast agent 412.

The optical parameters of the lens 403 are shown below in table 1.

TABLE 1

|  | Square root of A | Refractive index at the center |
|---|---|---|
| Wavelength: 0.550 um | 1.71 | 1.643 |

Also, in the 1310 nm wavelength, the working distance from the outer diameter of the sheath is 2.1 mm, and the working distance from the optical axis is 2.5 mm.

Figure 5:
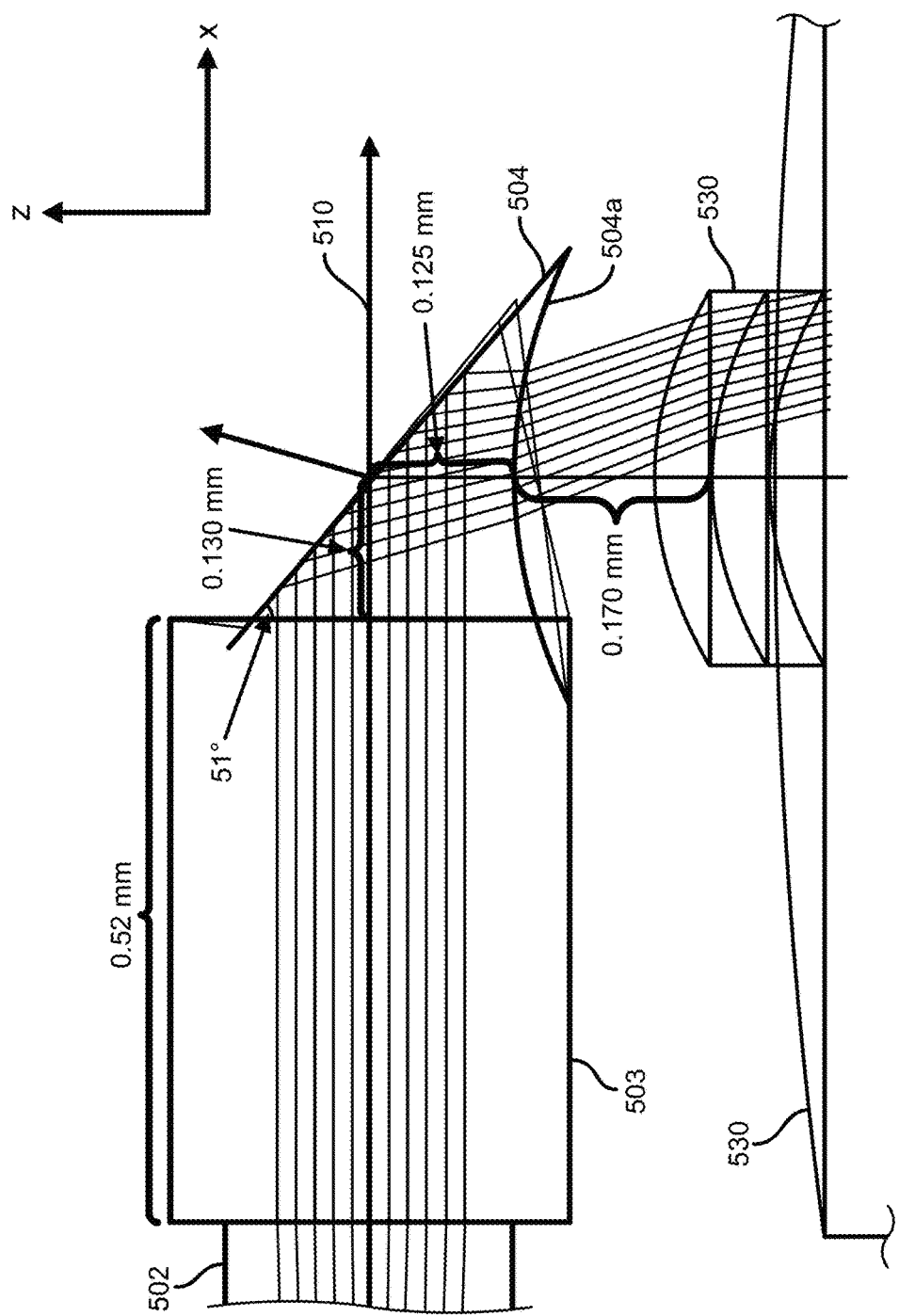
FIG. 5 illustrates some measurements of an example embodiment of a lens and a light-reflecting component.

FIG. 5 illustrates some measurements of an example embodiment of a lens 503 and a light-reflecting component 504. The lens 503, the sheath 530, and the second light-guiding component 502 have the same parameters as the lens 403, the sheath 430, and the second light-guiding component 402 in FIGS. 4A-D. Along the optical axis 510, the light-reflecting component is approximately 0.130 mm long in a direction that is parallel to the longitudinal axis of the lens 503 and is approximately 0.125 mm long in a direction that is orthogonal to the longitudinal axis of the lens 503. At the center of the curvature, the light-reflecting component 504 is approximately 0.170 mm from the sheath 530. The sheath 230 has an inner diameter of approximately 0.59 mm, with a wall thickness of approximately 0.1 mm.

The light-exiting surface 504a of the light-reflecting component 504 has a radius of approximately −0.6 mm (concave) in the tangential direction (the x-z plane in FIG. 5). The cylindrical surface of the prism 504 has the center of curvature at the position where the line that connects the reflecting surface of the prism to the center of the curvature is perpendicular to the optical axis 510.

Also, in some embodiments, the cylindrical surface of the prism 504 is configured such that its center of radius lies on the extension of the chief ray reflected by the light-reflecting surface of the prism 504. This configuration can reduce off-axis incidence to the light-exiting surface 504a and, therefore, reduce the aberration.

Figure 6:
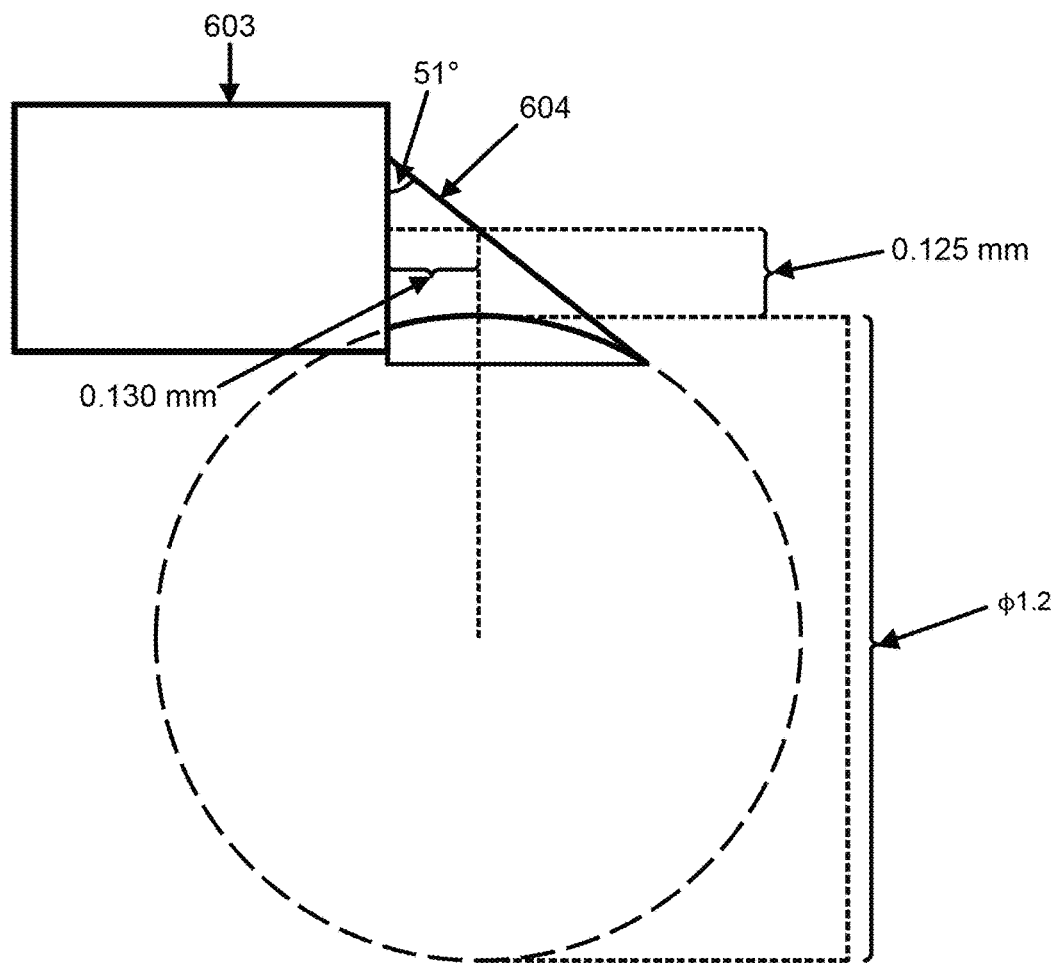
FIG. 6 illustrates some measurements of an example embodiment of a lens and a light-reflecting component.

FIG. 6 illustrates some measurements of an example embodiment of a lens 603 and a light-reflecting component 604. The lens 603 may have the same parameters as the lens 403 in FIGS. 4A-D or the lens 503 in FIG. 5. Also, FIG. 6 illustrates a circle that has a curvature that matches the curvature of the light-reflecting component 604. The circle has a diameter of 1.2 mm.

FIGS. 7A-7E illustrate an example embodiment of an optical probe 700 and a sheath 730. Some of the measurements of this example embodiment of an optical probe may be the same as the measurements of the lenses and the light-reflecting components that are shown in FIG. 5 or 6. FIG. 7A shows a perspective view of the embodiment of the optical probe 700. The optical probe 700 includes a first light-guiding component 701, a second light-guiding component 702, a lens 703, and a light-reflecting component 704.

FIG. 7B illustrates a view of the optical probe 700 from the x-y plane in FIG. 7A. FIG. 7B shows some of the measurements of the lens 703 and the light-reflecting component 704.

FIG. 7C illustrates a view of the optical probe 700 from the x-z plane in FIG. 7A. FIG. 7C shows some of the measurements of the second light-guiding component 702, the lens 703, and the light-reflecting component 704.

FIG. 7D illustrates a view of the optical probe 700 from the perspective of line CD in FIG. 7A. FIG. 7D shows some of the measurements of the second light-guiding component 702, the lens 703, and the light-reflecting component 704.

FIG. 7E illustrates a view of the optical probe 700 from the perspective of line CD in FIG. 7A. FIG. 7E shows some of the measurements of the second light-guiding component 702, the lens 703, and the light-reflecting component 704.

Figure 8:
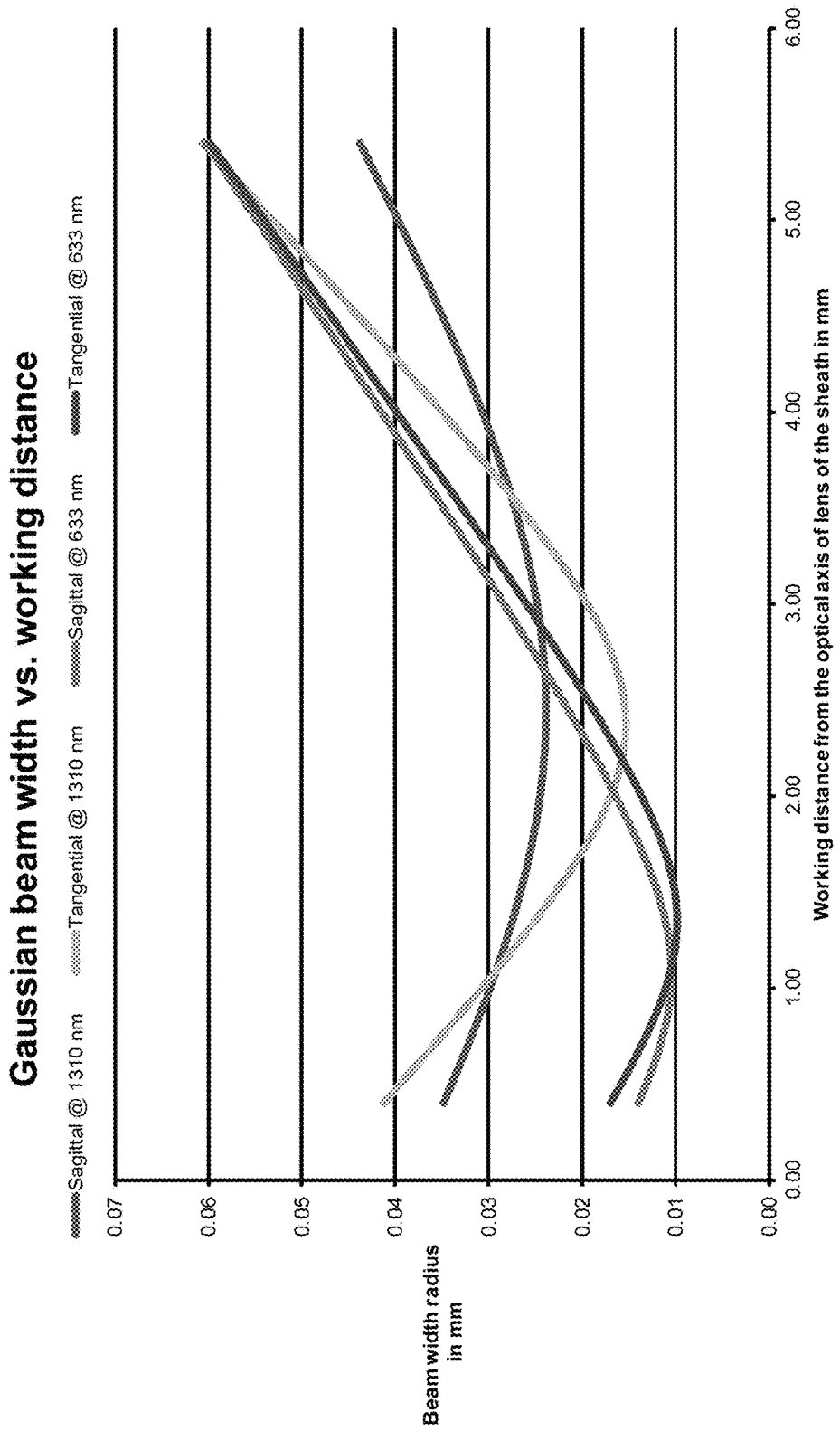
FIG. 8 illustrates the Gaussian beam width of the optical beam width radius versus the working distance from the optical axis of the optical probe for the example embodiment of an optical probe and a sheath that is illustrated in FIGS. 7A-7E.
Figure 9:
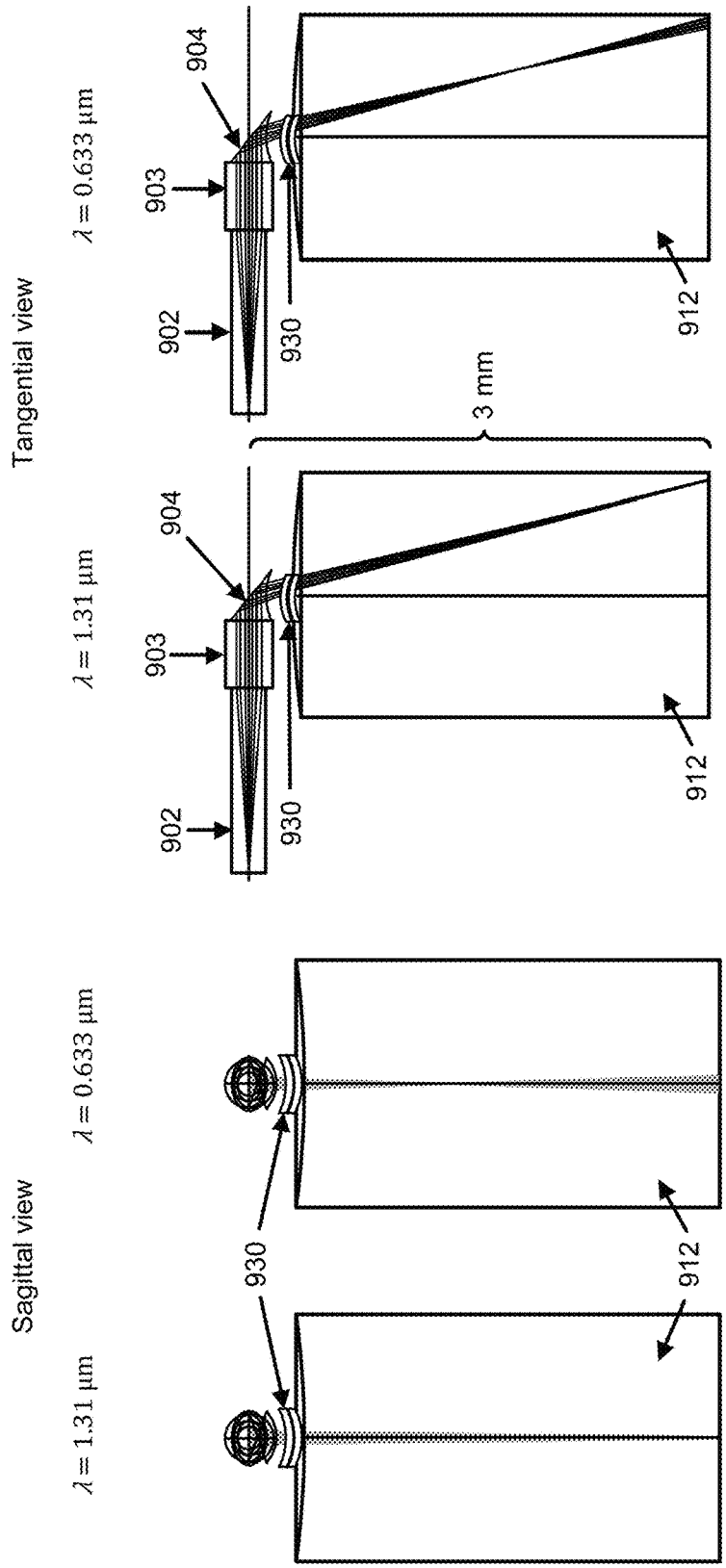
FIGS. 9A-D illustrate sagittal views and tangential views of an example embodiment of an optical probe and a sheath.

FIG. 8 illustrates the Gaussian beam width of the optical beam width radius versus the working distance from the optical axis of the optical probe for the example embodiment of an optical probe and a sheath that is illustrated in FIGS. 7A-7E. FIG. 8 shows that, in the 1.31 µm wavelength, the beams in both the tangential direction and the sagittal direction focus at a similar working distance (~2.5 mm) from the optical axis of the lens. FIG. 8 also shows that, in the 0.633 µm wavelength, the beams in both the tangential direction and the sagittal direction focus at a similar working distance (~1.2 mm) from the optical axis of the lens. This example embodiment of an optical probe essentially corrects the astigmatism in both the 1.31 μm beam and the 0.633 μm beam. The focal shift between the 0.633 μm and the 1.31 μm wavelengths that is due to chromatic aberration is about 1.3 mm.

FIGS. 9A-D illustrate sagittal views and tangential views of an example embodiment of an optical probe and a sheath. The structural configuration of this embodiment is similar to that of FIGS. 4A-D. The difference is that the lengths of the GRIN lens and the spacers are optimized to have a working distance of 3 mm from the optical axis of the lens 903. In this embodiment, light that has passed through a double-clad fiber that has a numerical aperture of 0.09 passes through a coreless fiber 902 (e.g., fused silica) that is approximately 1 mm long and then enters the lens 903, which is a GRIN lens that has a length of 0.5 mm. The light exits the lens 903 and is reflected by the reflecting surface of a prism 904, which has a refractive index of 1.52 and a tilt angle of 50±2° (The reflecting surface of the prism 904 has an angle such that the chief ray from the lens 903 has incident angle of 50±2°.). Also, the light-exiting surface of the prism 904 has a radius of approximately −0.6 mm in the tangential direction.

Then the light passes through a cylindrical surface of the exit surface of the prism 904, which has an optical power only in the tangential direction, and then passes through a sheath 930, which has an optical power only in the sagittal direction. The sheath 930 has inner diameter of approximately 0.5 mm and a wall thickness of approximately 0.1 mm. In air, the chief ray has an incident angle of 20° to the normal of the sheath 930. The light then passes through a contrast agent 912, which has a refractive index of 1.45 (n=1.45).

Figure 10:
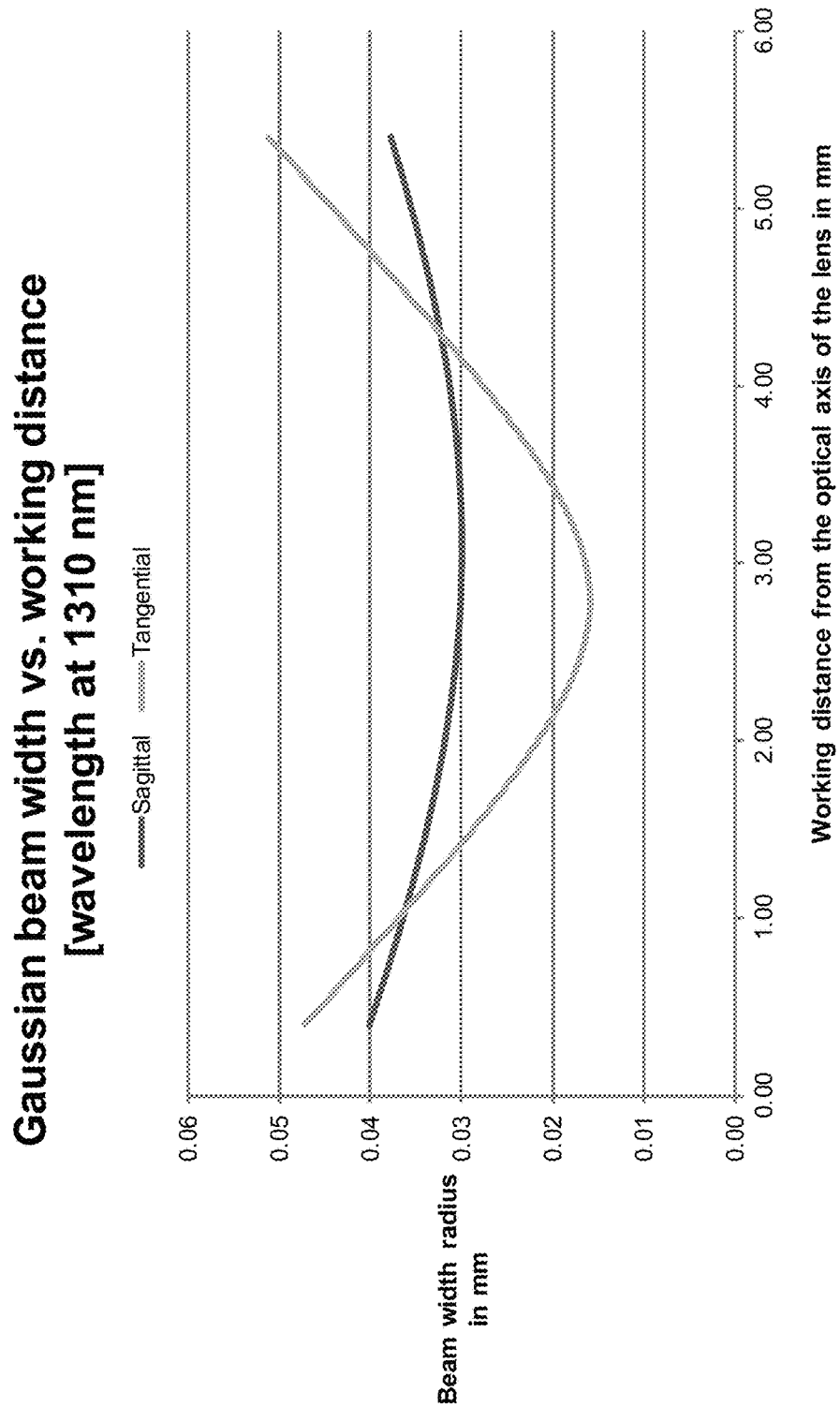
FIG. 10 illustrates the Gaussian beam width of the optical beam width radius versus the working distance from the optical axis of the optical probe for the example embodiment of an optical probe and a sheath that is illustrated in FIGS. 9A-D.

FIG. 10 illustrates the Gaussian beam width of the optical beam width radius versus the working distance from the optical axis of the optical probe for the embodiment of an optical probe and a sheath that is illustrated in FIGS. 9A-D. FIG. 10 shows that, in the 1.31 μm wavelength, the beams in both the tangential direction and the sagittal direction focus at a similar distance (~3 mm) from the optical axis of the lens.

Figure 11:
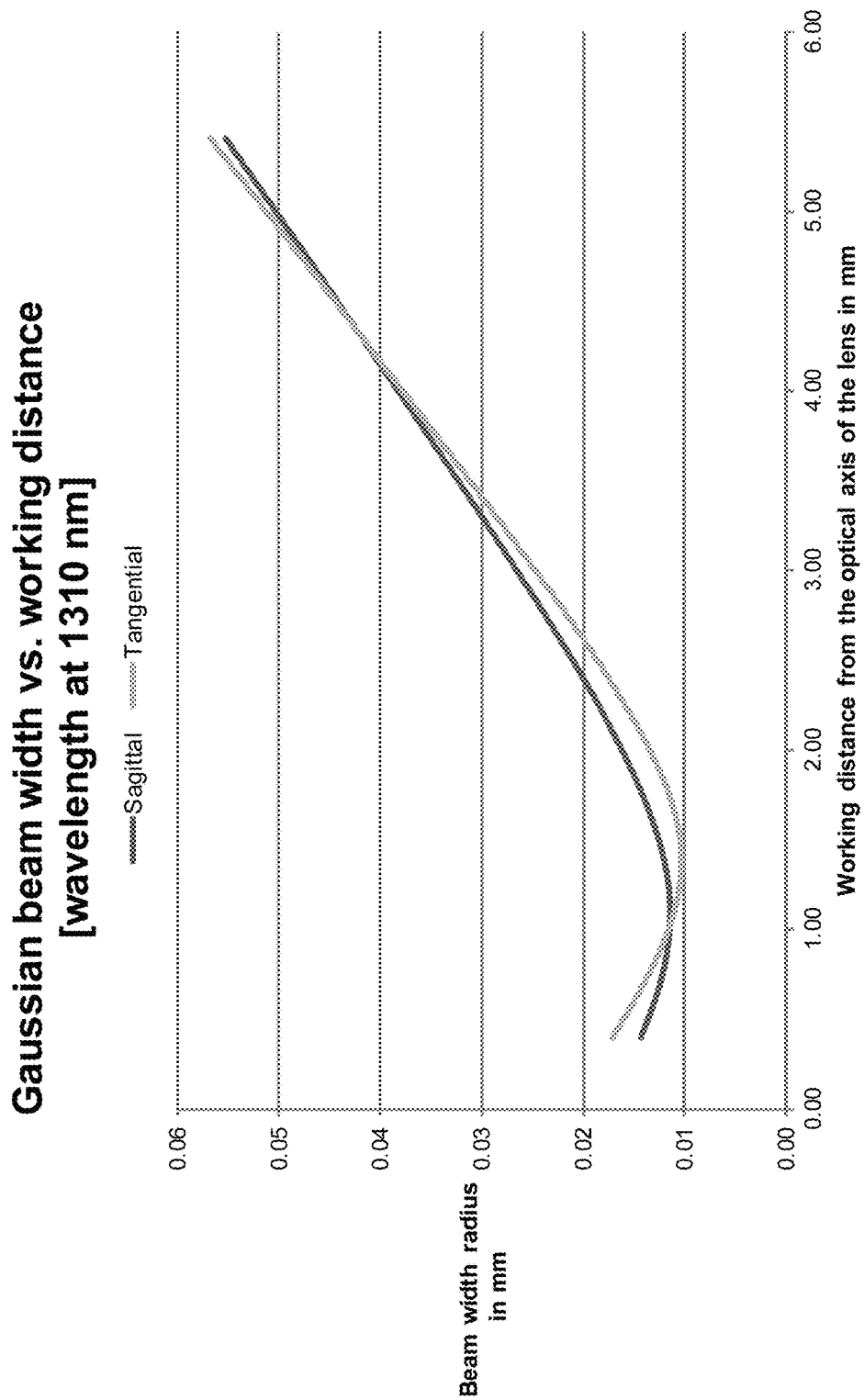
FIG. 11 illustrates the Gaussian beam width of the optical beam width radius versus the working distance from the optical axis of the optical probe for an example embodiment of an optical probe.

FIG. 11 illustrates the Gaussian beam width of the optical beam width radius versus the working distance from the optical axis of the optical probe for an example embodiment of an optical probe. The structural configuration of this embodiment of an optical probe is similar to that of FIGS. 4A-D. The difference is that the lengths of the GRIN lens and the spacer are optimized such that the working distance of this embodiment is 1.5 mm from the optical axis of the lens. In this embodiment, light that has passed through a double-clad fiber that has a numerical aperture of 0.09 passes through a coreless fiber (e.g., fused silica) that is 1.1 mm long and then enters a lens, which is a GRIN lens that has a length of 0.5 mm and a diameter of 350 μm. The other parameters of the lens are shown in Table 1.

The light exits the lens and is reflected by the reflecting surface of a prism, which has a refractive index of 1.52 and a tilt angle of 50±2°. Accordingly, the reflecting surface of the prism has an angle such that the chief ray from the lens has an incident angle of 50±2°. Also, the light-exiting surface of the prism has a radius of −0.6 mm in the tangential direction. Then the light passes through an exit surface of the prism, which is a cylindrical surface and has an optical power only in the tangential direction, and then passes through a sheath, which has an optical power only in the sagittal direction. In air, the chief ray has an incident angle of 14° to the sheath. The sheath has inner diameter of approximately 0.5 mm, a wall thickness of approximately 0.1 mm, and a refractive index of 1.5 (n=1.5).

FIG. 11 shows that, in the 1.31 μm wavelength, the beams in both the tangential direction and the sagittal direction focus at approximately 1 mm from the optical axis of the optical probe.

Figure 12:
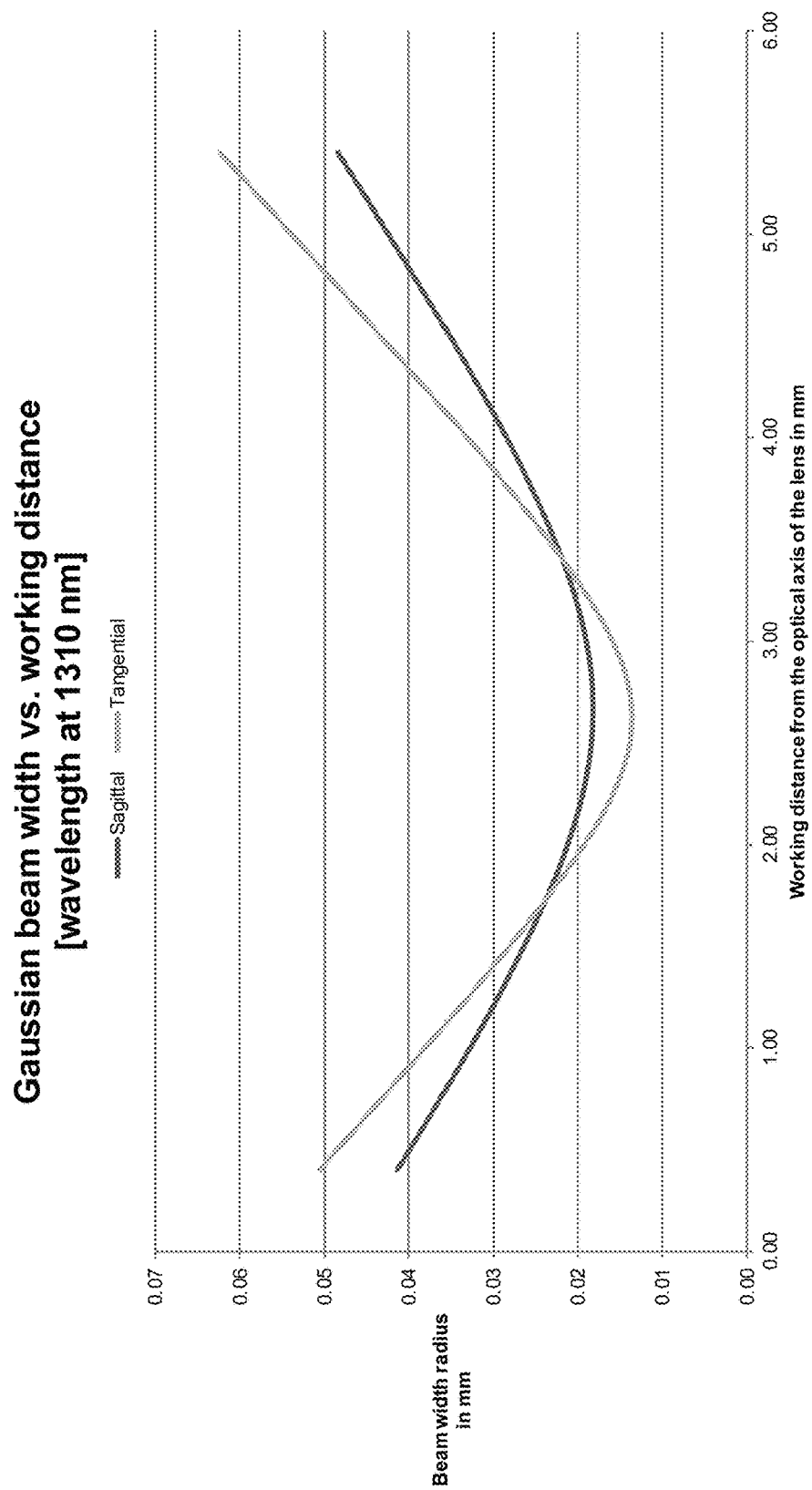
FIG. 12 illustrates the Gaussian beam width of the optical beam width radius versus the working distance from the optical axis of the optical probe for an example embodiment of an optical probe.

FIG. 12 illustrates the Gaussian beam width of the optical beam width radius versus the working distance from the optical axis of the lens for an example embodiment of an optical probe. The structural configuration of this embodiment is similar to that of FIGS. 4A-D. The difference is that the length and refractive-index profile of the GRIN lens and the length of the spacer are optimized to obtain a desired working distance of 2.5 mm from the optical axis of the lens in the 1.31 μm wavelength. In this embodiment, light that has passed through a double-clad fiber that has a numerical aperture of 0.09 passes through a length of 1.2 mm coreless fiber (e.g., fused silica) and then enters a lens, which is a GRIN lens that has a length of 0.3 mm and a diameter of 250 μm. The other parameters of the lens are shown in Table 2.

TABLE 2

| | Square root of A | Refractive index at the center |
|---|---|---|
| Wavelength: 0.550 um | 2.319 | 1.643 |

The light exits the lens and is reflected by the reflecting surface of a prism, which has a refractive index of 1.52 and a tilt angle of 50±2° in this example. Accordingly, the reflecting surface of the prism has an angle such that the chief ray from the lens has an incident angle of 50±2°. Also, the light-exiting surface of the prism has a radius of −0.55 mm in the tangential direction. Then the light passes through an exiting surface of the prism, which is a cylindrical surface and has an optical power only in the tangential direction, and then passes through a sheath, which has an optical power only in the sagittal direction. In air, the chief ray has an incident angle of 20° to the sheath in the tangential direction. The sheath has inner diameter of approximately 0.5 mm and a wall thickness of approximately 0.1 mm with a refractive index of 1.5 (n=1.5). The light then passes through a contrast agent, which has a refractive index of 1.45 (n=1.45).

FIG. 12 shows that, in the 1.31 μm wavelength, the beams in both the tangential direction and the sagittal direction focus at approximately 2.5 mm from the optical axis of the optical probe.

Figure 13:
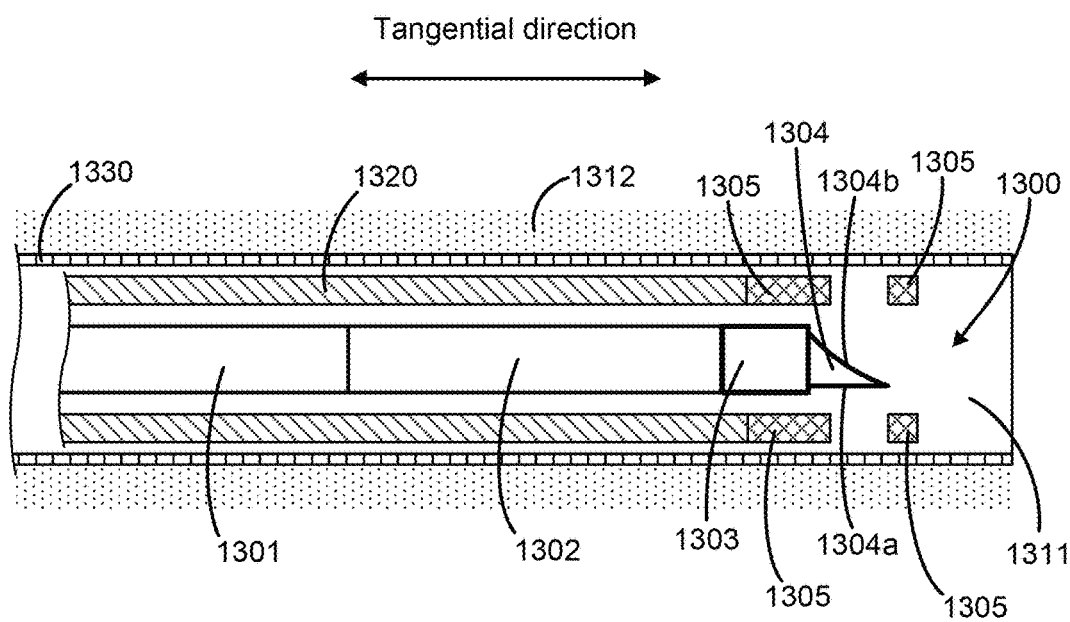
FIG. 13 illustrates a partially-cutaway view of an example embodiment of an optical probe, a drive cable, and a sheath.

FIG. 13 illustrates a partially-cutaway view of an example embodiment of an optical probe 1300, a drive cable 1320, and a sheath 1330. The optical probe 1300 includes a first light-guiding component 1301, a second light-guiding component 1302 (e.g., a glass rod), a lens 1303, a light-reflecting component 1304, and a protector 1305. In this embodiment, the optical probe 1300 corrects the astigmatism by introducing an optical power on the reflecting surface 1304b of the light-reflecting component 1304. In some embodiments, the light-exiting surface 1304a of the light-reflecting component 1304 also introduces an optical power.

Figure 14:
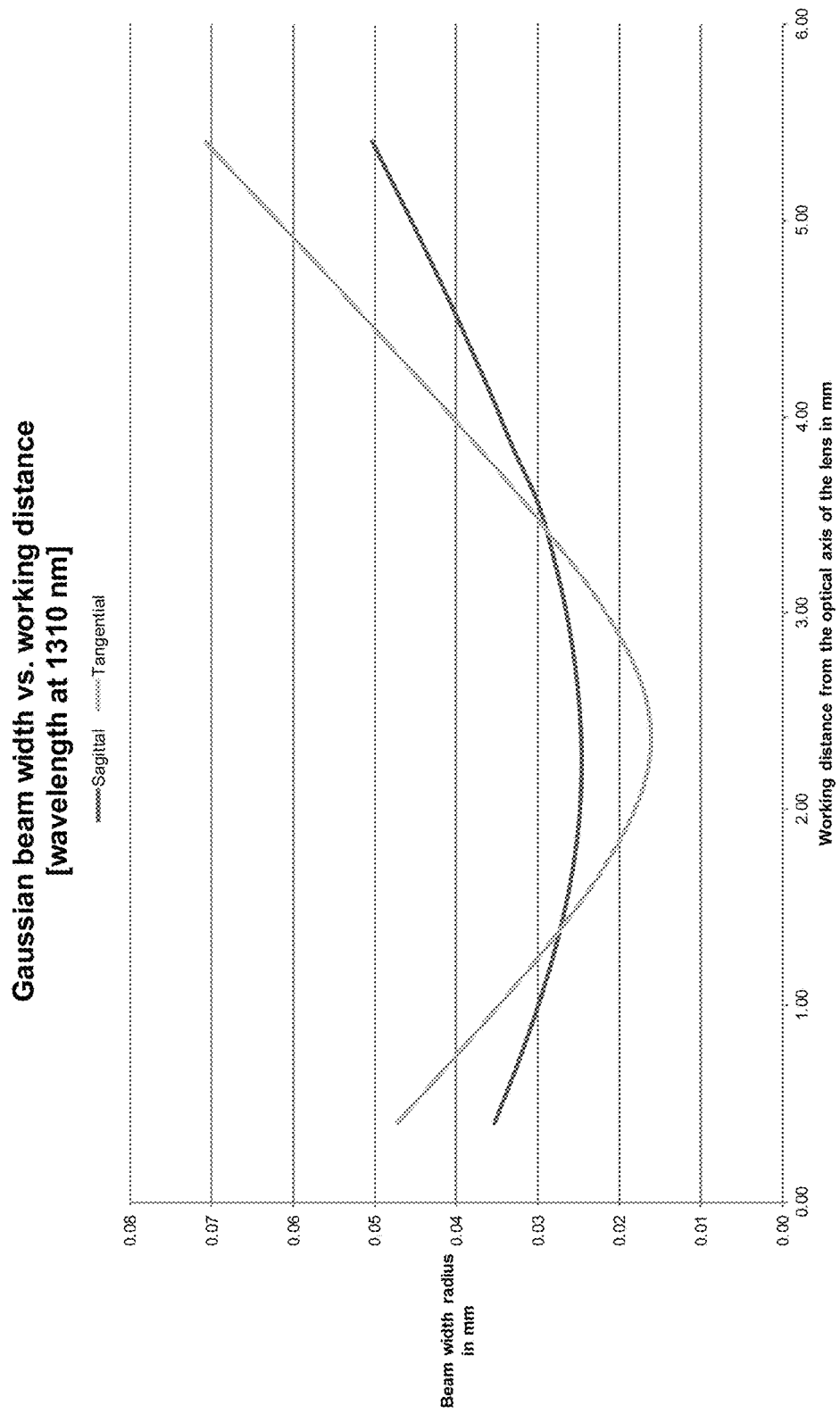
FIG. 14 illustrates the Gaussian beam width of the optical beam width radius versus the working distance from the optical axis of the optical probe for an example embodiment of an optical probe.

FIG. 14 illustrates the Gaussian beam width of the optical beam width radius versus the working distance from the optical axis of the optical probe for an example embodiment of an optical probe. Like FIG. 13, this embodiment of an optical probe corrects the astigmatism by introducing an optical power on a reflecting surface of a light-reflecting component. The refractive index profile, the length of the GRIN lens, and the length of the spacer are optimized to achieve the desired working distance. This embodiment has a working distance of ~2.5 mm from the optical axis of the lens at the 1.31 µm wavelength.

In this embodiment, light that has passed through a double-clad fiber that has a numerical aperture of 0.1 passes through a length of 1.15 mm coreless fiber (e.g., fused silica) and then enters a lens, which is a GRIN lens that has a length of 0.3 mm and a diameter of 250 µm. The other parameters of the GRIN lens are described in Table 2.

The light exits the lens and is reflected by the reflecting surface of a prism, which has a refractive index of 1.52 and a tilt angle of 50±2°. Accordingly, the reflecting surface of the prism has an angle such that the chief ray from the lens has an incident angle of 50±2°. Also, the light-reflecting surface of the prism has a radius of 5.5 mm (concave) in the tangential direction. The radius of curvature of the reflecting surface of the prism is optimized to correct the astigmatism caused by the sheath. The negative optical power of the curved reflecting surface in the tangential direction is approximately the same as the negative optical power of the sheath in the sagittal direction. Then the light passes through a flat surface of the exit surface of the prism and passes through the sheath, which has an optical power only in the sagittal direction. In air, the chief ray has an incident angle of 20° to the sheath in the tangential direction. The sheath has an inner diameter of approximately 0.5 mm, a wall thickness of 0.1 mm, and a reflective index of 1.5 (n=1.5). The light then passes through a contrast agent, which has a refractive index of 1.45 (n=1.45). Also, the inner media is air with a refractive index of 1 (n=1) and the outer media is a contrast agent with a refractive index of 1.45 (n=1.45).

FIG. 14 shows that, in the 1.31 µm wavelength, the beams in both the tangential direction and the sagittal direction focus at approximately 2.15 mm from the optical axis of the optical probe.

Figure 15:
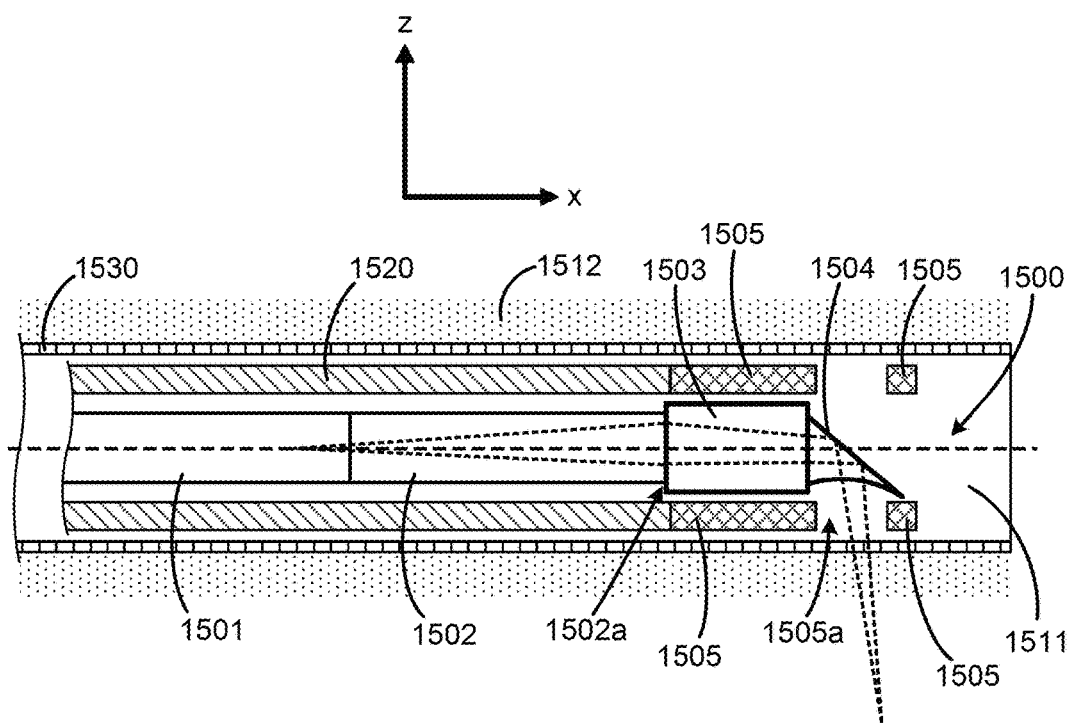
FIG. 15 illustrates a partially-cutaway view of an example embodiment of an optical probe, a drive cable, and a sheath.

FIG. 15 illustrates a partially-cutaway view of an example embodiment of an optical probe 1500, a drive cable 1520, and a sheath 1530. The optical probe 1500 includes a first light-guiding component 1501, a second light-guiding component 1502, a lens 1503, a light-reflecting component 1504, and a protector 1505. The protector 1505 has a window 1505a. The optical probe 1500 is configured such that at least some of the light that exits the light-reflecting component 1504 travels through the window 1505a. In this embodiment, the second light-guiding component 1502 is a glass rod that has an outer diameter of 250 µm, and the lens 1503 is a GRIN lens that has an outer diameter of 350 µm. The step 1502a between the second light-guiding component 1502 and the lens 1503 can be used to register the z-axis position of the optical probe 1500 such that a beam of light can pass through the window 1505a without vignetting.

Figure 16A:
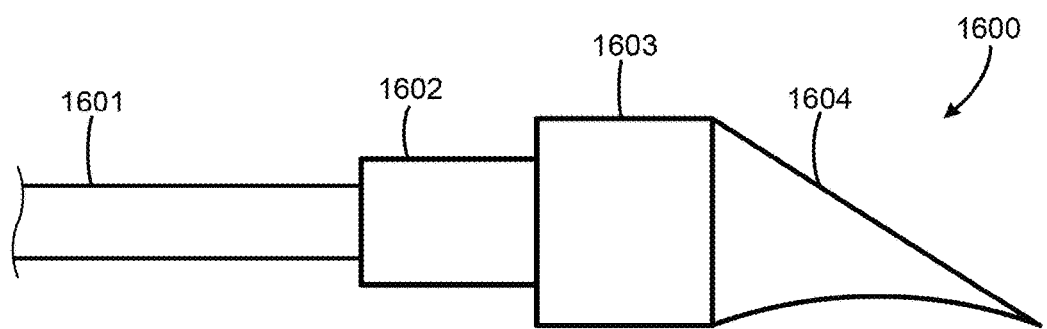
FIG. 16A illustrates an example embodiment of an optical probe.

FIG. 16A illustrates an example embodiment of an optical probe 1600. The optical probe 1600 includes a first light-guiding component 1601, a second light-guiding component 1602, a lens 1603, and a light-reflecting component 1604. In this embodiment, the diameter of the first light-guiding component 1601 is smaller than the diameter of the second light-guiding component 1602. Also, the diameter of the second light-guiding component 1602 is smaller than the diameter of the lens 1603. Furthermore, when used with a drive cable (e.g., the drive cable 220 in FIG. 2), the inner diameter of the drive cable may be greater than both the outer diameter of the first light-guiding component 1601 and the outer diameter of the second light-guiding component 1602. Additionally, the inner diameter of the drive cable may be less than the outer diameter of the lens 1603 and less than an inner diameter of a protector.

Figure 16B:
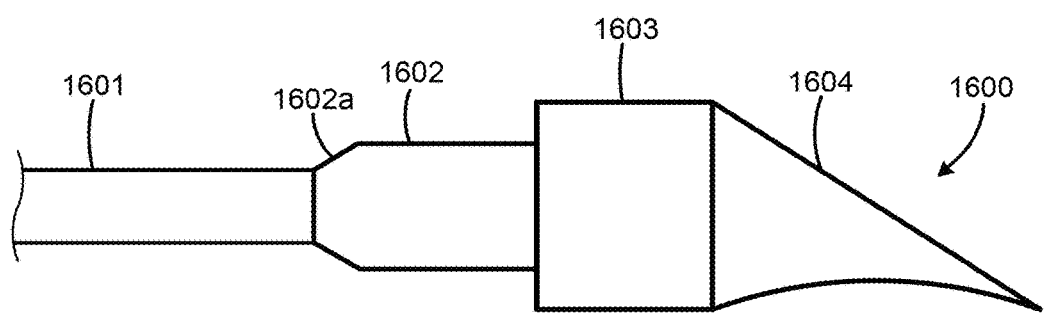
FIG. 16B illustrates an example embodiment of an optical probe.

FIG. 16B illustrates an example embodiment of an optical probe 1600. The optical probe 1600 includes a first light-guiding component 1601, a second light-guiding component 1602, a lens 1603, and a light-reflecting component 1604. In this embodiment, the second light-guiding component 1602 has a taper 1602a near the attachment to the first light-guiding component 1601.

Figure 16C:
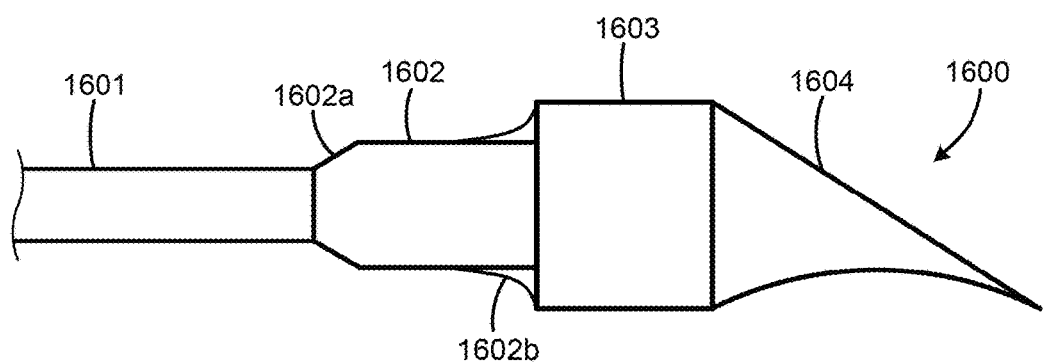
FIG. 16C illustrates an example embodiment of an optical probe.

FIG. 16C illustrates an example embodiment of an optical probe 1600. The optical probe 1600 includes a first light-guiding component 1601, a second light-guiding component 1602, a lens 1603, and a light-reflecting component 1604. In this embodiment, the second light-guiding component 1602 has a taper 1602a near the connection to the first light-guiding component 1601. Also, the second light-guiding component 1602 is attached to the lens 1603 by a transparent epoxy 1602b, which forms a taper near the attachment point.

Figure 17:
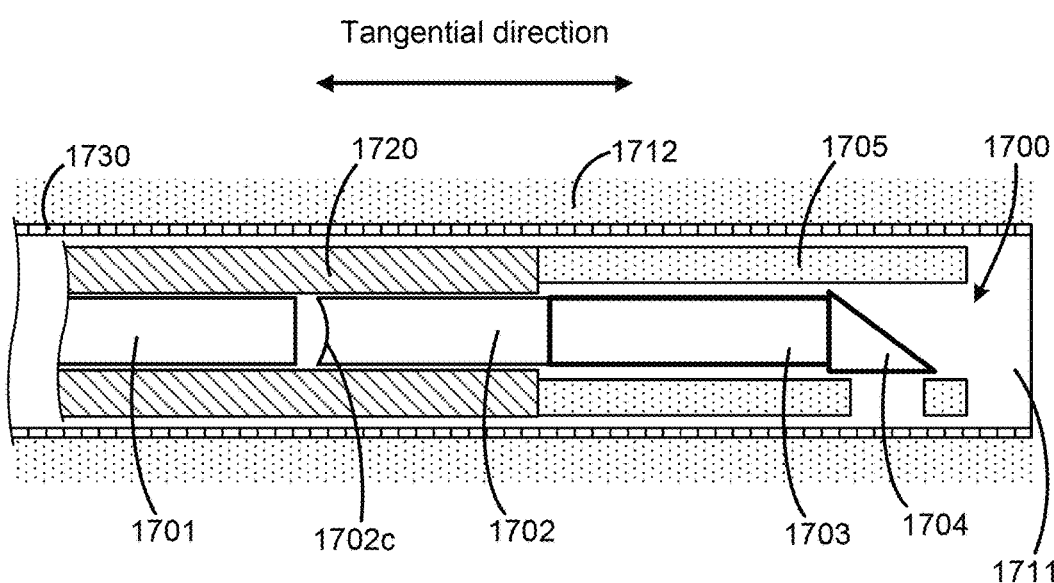
FIG. 17 illustrates a partially-cutaway view of an example embodiment of an optical probe, a drive cable, and a sheath.

FIG. 17 illustrates a partially-cutaway view of an example embodiment of an optical probe 1700, a drive cable 1720, and a sheath 1730. The optical probe 1700 includes a first light-guiding component 1701, a second light-guiding component 1702, a lens 1703, a light-directing component 1704, and a protector 1705. The second light-guiding component 1702 has a concave surface 1702c where light enters the second light-guiding component 1702. In this embodiment, the concave surface 1702c introduces an optical power in the tangential direction to compensate for the negative power of the sheath 1730 in the sagittal direction. In some embodiments, the tangential optical power of the concave surface 1702c is equal to the negative power of the sheath 1730 in the sagittal direction, for example as described below:

$$\phi_{sr,tan} = \phi_{sheath,sag},$$

$$\phi_{sr,tan} < 0, \text{ and}$$

$$\phi_{sheath,sag} < 0,$$

where $\phi_{sr,tan}$ is the optical power of the second light-guiding component 1702 in the tangential direction, and where $\phi_{sheath,sag}$ is the optical power of the sheath 1730 in the sagittal direction.

Figure 18:
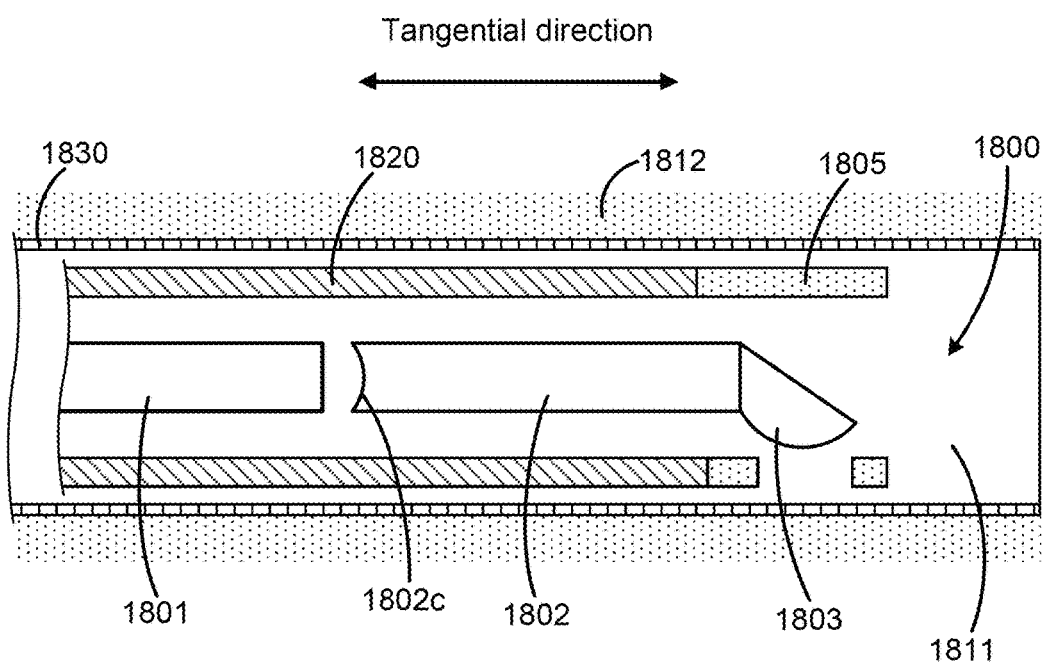
FIG. 18 illustrates a partially-cutaway view of an example embodiment of an optical probe, a drive cable, and a sheath.

FIG. 18 illustrates a partially-cutaway view of an example embodiment of an optical probe 1800, a drive cable 1820, and a sheath 1830. The optical probe 1800 includes a first light-guiding component 1801, a second light-guiding component 1802, a lens 1803, a light-reflecting component 1804, and a protector 1805. In this embodiment, the lens 1803 is a half-ball lens. The second light-guiding component 1802 has a concave surface 1802c where light enters the second light-guiding component 1802. The concave surface 1802c introduces an optical power in the tangential direction to compensate for the negative power of the sheath 1830 in the sagittal direction. In some embodiments, the tangential optical power of the concave surface 1810 is equal to the negative power of the sheath 1830 in the sagittal direction.

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or."

The invention claimed is:
1. A device comprising:
a light-guiding component;
an optical component;

a light-reflecting component that is configured to receive light from the optical component and direct the light along a path; and a sheath that surrounds at least part of the optical component and at least part of the light-reflecting component and that has an optical power in the sagittal direction, wherein at least one of the optical component and/or the light-reflecting component has a negative optical power in the tangential direction, and wherein the negative optical power of the at least one of the optical component and/or the light-reflecting component in the tangential direction is essentially equal or approximately equal to the optical power of the sheath in the sagittal direction.

2. The device of claim 1, wherein the light-reflecting component has the negative optical power in the tangential direction.

3. The device of claim 2, wherein a light-reflecting surface of the light-reflecting component has the negative optical power in the tangential direction.

4. The device of claim 2, wherein an exiting surface of the light-reflecting component has the negative optical power in the tangential direction.

5. The device of claim 1, wherein the negative optical power in the tangential direction corrects an astigmatism in a wavelength of light for optical-coherence-tomography imaging and corrects an astigmatism in a wavelength of light for fluorescence excitation such that a mean focal distance of the wavelength of light for optical-coherence-tomography imaging is within 2 mm of a mean focal distance of the wavelength of light for fluorescence excitation.

6. The device of claim 1, wherein the negative optical power in the tangential direction corrects an astigmatism in a wavelength of light for optical-coherence-tomography imaging.

7. The device of claim 1, wherein the negative optical power in the tangential direction corrects an astigmatism in a wavelength of light for fluorescence excitation.

8. The device of claim 1, wherein the optical component has the negative optical power in the tangential direction.

9. The device of claim 8, wherein the optical component includes a lens and another light-guiding component.

10. The device of claim 9, wherein a light-entrance surface of the another light-guiding component has the negative optical power in the tangential direction.

11. The device of claim 9, wherein the another light-guiding component is a glass rod or a coreless fiber.

12. The device of claim 1, wherein the optical component includes a GRIN lens or a ball lens.

13. A device comprising:
a sheath; and
an optical probe that includes:
a first light-guiding component,
an optical component, and
a light-reflecting component,
wherein the optical probe has a negative optical power in the tangential direction,
wherein the sheath surrounds at least part of the optical component and at least part of the light-reflecting component, and the sheath has an optical power in the sagittal direction, and
wherein at least one of the optical component and/or the light-reflecting component has the negative optical power in the tangential direction, and the negative optical power is essentially equal or approximately equal to the optical power of the sheath in the sagittal direction.

14. The device of claim 13, wherein the optical component includes an entrance surface,
wherein light enters the optical component through the entrance surface, and
wherein the entrance surface has the negative optical power in the tangential direction.

15. The device of claim 14, wherein the optical component includes a glass rod.

16. The device of claim 13, wherein the light-reflecting component has the negative optical power in the tangential direction.

17. The device of claim 16, wherein the light-reflecting component has a light-exiting surface that has the negative optical power in the tangential direction.

18. The device of claim 16, wherein the light-reflecting component has a light-reflecting surface that has the negative optical power in the tangential direction.

19. A device comprising:
an optical component;
a light-reflecting component; and
a sheath that surrounds at least part of the optical component and at least part of the light-reflecting component and that has an optical power in the sagittal direction,
wherein at least one of the optical component and/or the light-reflecting component has an optical power in the tangential direction or the sagittal direction, and
wherein the optical power of the at least one of the optical component and/or the light-reflecting component:
(i) in the tangential direction is essentially equal or approximately equal to the optical power of the sheath in the sagittal direction; and/or
(ii) compensates in the tangential direction for the optical power of the sheath to correct for aberration.

20. The device of claim 19, wherein the light-reflecting component is a prism.

21. The device of claim 20, wherein the optical component includes a GRIN lens.

22. A device comprising:
a light-guiding component;
an optical component;
a light-reflecting component that is configured to receive light from the optical component and direct the light along a path; and
a sheath that has a negative optical power in the sagittal direction,
wherein at least the optical component has an asymmetric optical power and the optical power in the sagittal direction is positive, and
wherein a net optical power of the positive optical power in the sagittal direction of the optical component and of the negative optical power in the sagittal direction of the sheath is substantially zero.

23. The device of claim 22, wherein the light reflecting component also has an asymmetric optical power and the optical power in the sagittal direction is positive.

24. The device of claim 22, wherein a light-entrance surface of the optical component has the asymmetric optical power and the optical power in the sagittal direction is positive.

25. A device comprising:
a light-guiding component;
an optical component;

a light-reflecting component that is configured to receive light from a lens and direct the light along a path;

a sheath that surrounds at least part of the optical component and at least part of the light-reflecting component and that has an optical power in the sagittal direction; and means for producing a negative optical power in the tangential direction, wherein the negative optical power in the tangential direction is essentially equal or approximately equal to the optical power of the sheath in the sagittal direction.

26. The device of claim 25, wherein the optical component includes a lens.

27. The device of claim 1, wherein one or more of the following:
   (i) the tangential direction is a direction along a first plane that includes a chief ray of light from, or reflected by, the light-reflecting component, and an optical axis of the light-guiding component;
   (ii) the sagittal direction is a direction along a second plane that is perpendicular to the first plane, and includes the chief ray; and
   (iii) the optical component and the light-reflecting component are separate or distinct from each other.

28. The device of claim 13, wherein one or more of the following:
   (i) the tangential direction is a direction along a first plane that includes a chief ray of light from, or reflected by, the light-reflecting component, and an optical axis of the first light-guiding component;
   (ii) the sagittal direction is a direction along a second plane that is perpendicular to the first plane, and includes the chief ray; and
   (iii) the optical component and the light-reflecting component are separate or distinct from each other.

29. The device of claim 19, wherein one or more of the following:
   (i) the tangential direction is a direction along a first plane that includes a chief ray of light from, or reflected by, the light-reflecting component, and an optical axis of one or more of the device, the optical component and/or the light-reflecting element;
   (ii) the sagittal direction is a direction along a second plane that is perpendicular to the first plane, and includes the chief ray; and
   (iii) the optical component and the light-reflecting component are separate or distinct from each other.

30. The device of claim 25, wherein one or more of the following:
   (i) the tangential direction is a direction along a first plane that includes a chief ray of light from, or reflected by, the light-reflecting component, and an optical axis of the light-guiding component;
   (ii) the sagittal direction is a direction along a second plane that is perpendicular to the first plane, and includes the chief ray; and
   (iii) the optical component and the light-reflecting component are separate or distinct from each other.

* * * * *